United States Patent [19]

Hoeft

[11] Patent Number: 5,687,726

[45] Date of Patent: Nov. 18, 1997

[54] PROCESS FOR DETERMINING THE VOLUME OF BLOOD IN CIRCULATION

[76] Inventor: Andreas Hoeft, Planckstrasse 13, D-3400 Gottingen, Germany

[21] Appl. No.: 415,583

[22] Filed: Apr. 3, 1995

Related U.S. Application Data

[63] Continuation of Ser. No. 50,270, filed as PCT/DE92/00796, Sep. 12, 1992, abandoned.

[30] Foreign Application Priority Data

Sep. 13, 1991 [DE] Germany .................. 41 30 931.6

[51] Int. Cl.$^6$ .................................................. A61B 6/00
[52] U.S. Cl. ...................... 128/654; 128/633; 128/691
[58] Field of Search ...................... 128/653.1, 654, 128/633, 691, 692, 694, 666

[56] References Cited

U.S. PATENT DOCUMENTS

| | | | |
|---|---|---|---|
| 4,197,836 | 4/1980 | Wagner et al. | 128/654 |
| 4,811,741 | 3/1989 | Shell et al. | 128/691 |
| 4,819,646 | 4/1989 | Cheung et al. | 128/633 |
| 5,230,343 | 7/1993 | Guberek et al. | 128/691 |
| 5,253,649 | 10/1993 | Gross et al. | 128/691 |

FOREIGN PATENT DOCUMENTS

| | | |
|---|---|---|
| 0 359 972 | 8/1989 | European Pat. Off. . |
| 0 359 206 | 3/1990 | European Pat. Off. . |
| 1498534 | 7/1972 | Germany . |
| 2 141 604 | 3/1973 | Germany . |
| 2622726 | 3/1979 | Germany . |

OTHER PUBLICATIONS

Hoeft et al.—Measurement of Coronary Blood Flow by a Double Fiberoptic System with Microcomputer–Aided Deconvolution of Transcoronary Dye Dilution Tracings (1983), pp. 216–220.

Fearnot et. al—Calculation of Catheter–Based Saline Dilution Cardiac Output (1985), pp. 490–494.

Haneda et al.—A Method Of Measurement Of Total Circulating Blood Volume Using Indocyanine Green (1986), pp. 49–56.

Cole et al—Rapid Assessment of Cardiac Output and Central Blood Volumes From Indicator Dilution Curves Without Precalculation Using Programmable Calculators (1980), pp. 105–112.

*Primary Examiner*—Brian L. Casler
*Attorney, Agent, or Firm*—Richard G. Lione; Brinks Hofer Gilson & Lione

[57] ABSTRACT

A process of rapidly determining the blood circulation volume in a patient during surgery. Blood circulation volume is determined from circulation transport functions based on the evaluation of a compartmental analysis of a dye dilution curve. The information content of the entire dye dilution curve is utilized for the calculation of the parameters of the circulation transport function.

8 Claims, 4 Drawing Sheets

PROCESS FOR DETERMINING THE VOLUME OF BLOOD IN CIRCULATION

This application is a continuation, of application Ser. No. 08/050,270, filed as PCT/DE92/00796, Sep. 12, 1992, now abandoned.

FIELD OF THE INVENTION

The Invention relates generally to a process and apparatus for determining the circulating blood volume. It relates particularly to a process and apparatus of the type wherein a known amount of indicator dye is injected into the circulating blood, the resulting dye concentration in the circulating blood is measured optically, and blood volume is calculated either from the known amount of indicator dye injected and the dye concentration time course or from the blood volume flow and the media transit time of the indicator dye determined from the dye concentration time course.

BACKGROUND OF THE INVENTION

Normal functioning of the cardiac circulation system is critically dependent on filling of the blood vessels with an adequate blood volume. A deficiency in blood, just as well as an overfilling, can lead to a life-threatening circulatory failure. In intensive medicine as well as perioperative anesthesiological therapy an essential goal is assuring adequate filling of the circulatory system despite, in part, great losses of blood and/or of fluids. Therapeutic decision making regarding circulating blood volume is presently based on indirect magnitudes, such as blood pressure, heart rate and central venous pressure, because direct measurements of the blood volume are technically expensive and, under clinical conditions, hardly feasible.

A further field of application for the measurement of the blood volume is that of competitive sports, in which the knowledge of the influences of training methods, clothing and nutrition is evaluated for optimization of the performance and endurance of the athletes. In this area consideration is given only to measuring processes that require but a short measuring time and do not influence the measurement result by the measuring method itself.

There are radionuclide methods available for measuring circulating blood volume. However, those available are not usable in the intensive medical and perioperative areas, nor are they applicable in competitive sports, because of the radiation burden for the patient or the competitive athlete and other personnel, as well as because of the expense.

Alternatively, the blood volume can also be determined with the aid of indicator dilution methods and dyes as indicators. Here there is used mostly indocyanine green (ICG) which, after injection into the circulation, is completely bound to plasma proteins and, therefore, does not leave the vascular system. The measuring methodology is based on the principle of mass preservation, i.e., the principle that after injection of a known amount of ICG and distribution of the ICG in the total blood volume, it is possible to determine the distribution volume for the indicator that corresponds to the blood volume from the resulting concentration.

The concentration is not directly measurable, however, since the dye is already excreted by the liver before homogeneous distribution in the circulation has come about. In a normally functioning liver, the half-value time of the ICG lies between 3 and 5 minutes. It is necessary, therefore, in order to reach a conclusion as to the virtual concentration present at the time point t=0, to take several blood samples over a period of at least 15 minutes after the injection in order to detect, from the drop in concentration, the elimination kinetics of the dye by the liver and, by means of back-extrapolation, mostly of the exponential type, to decide upon the ideal concentration for the time point of the injection.

This process, also, is clinically only conditionally usable. A great amount of time expenditure is necessary for the recovery and processing of the blood samples and, also, an appreciable amount of blood must be taken from the patient.

In a further development of the above-described process it was endeavored, therefore, to carry out the dye proof directly in the vascular system with the aid of fiber-optic catheters. After a bolus injection of ICG by means of a central venous catheter in the right atrium, and registration of the concentration time course in the aorta (therefore the main artery), there is obtained a typical time course of a dye dilution curve. After a first passage of the dye from the injection site through the lung circulation a rising of the concentration is again observed, which results from the recirculation of the indicator. Only after several circulation passages of the dye is it possible to assume sufficient distribution of the dye in the circulation; and only after this would it be possible from the slow, hardly visible decline of the indicator concentration to determine the elimination kinetics of the dye by the liver. The essential problem in this approach lies in that, on the one hand a sufficiently long time has to be waited before the distribution phase of the dye is finished while, on the other hand, the dye concentration becomes lower and lower with increasing time and, therefore, frequently the lower detection limit for fiber-optic dye measurement is passed.

Underlying the present invention is the problem of developing a process for determining the blood circulation volume in which the entire information content of the optically measured dye dilution curve is utilized for the calculation of the elimination kinetics.

SUMMARY OF THE INVENTION

An object of the present invention is to provide an improved process for determining the circulating blood volume.

Another object is to provide an apparatus for determining the circulating blood volume.

According to the process of the invention, calculation of the blood circulation volume from the circulation transport function is based on the evaluation of a compartmental analysis of the dye dilution curve. A substantial advantage over the in-vitro process mentioned at the outset lies in the fact that the process of the invention requires no taking of blood which, especially in the case of multiple determinations, can lead to not-inconsiderable blood losses for the patient. Likewise, the reduced time requirement is to be emphasized. A period of 3 to 4 minutes is sufficient as a measuring time duration after the dye injection, according to experience to date. In contrast, the in-vitro determination requires blood sampling over a period of at least 15 minutes. Furthermore, there the blood samples must be measured spectro-photometrically, which is expensive, and then evaluated. As a general rule, the result of the measurement with the in-vitro process would not be available for an hour after measuring.

The advantage of the process according to the invention over the also mentioned fiber-optic, dye detection approach, lies in the fact that the information content of the entire dye dilution curve is utilized for the calculation of the parameters of the circulation transport function. The dye elimination, which also takes place during the distribution phase is, accordingly, also covered with this solution.

In the known approaches for determining the blood circulation volume by means of fiber-optic dye detection it is endeavored, after decay of the distribution phase of the dye, to carry out a monoexponential extrapolation of the dye signal. Here it is a substantial disadvantage that the dye concentrations at this point in time are very low and can lie, in part, below the detection limit. Extrapolation in the later range of the dye dilution curve, therefore, involves great uncertainties. So far, a validation of this process does not exist.

For the calculation of the blood volume from the circulation transport functions according to the invention two alternatives are offered. In one, the circulation impulse response which would correspond to an ideal indicator injection at a time point of t=0 can be determined in an extremely short time. From the circulation impulse response there is determined, by retro-extrapolation or direct calculation from the parameters of the circulation transport function, the virtual dye concentration at the time point of t=0. The blood circulation volume is then calculated from the given amount of the injected indicator dye and the virtual dye concentration at the time point of t=0. In another, the mean transit time $m_{tr}$ which the indicator dye requires to pass through the circulation or a partial circulation can be determined. The blood volume is calculated from the volume flow and the mean transit time.

In the practical execution of the process, the first alternative is preferred. Here, too, there is a substantial advantage over the processes mentioned at the outset.

The problem with the conventional monoexponential retro-extrapolation technique lies in the definition of an injection time point, i.e. in the choice of a correct time axis on which the calculation with retro-extrapolation decisively depends. The dye injection, however, can occur only in finite time, so that as an auxiliary measure the mean injection time point must be defined as the reference time point. It is to be borne in mind, however, that at this time point the indicator has not yet reached the arterial vascular system, and from there the elimination of the indicator has not yet begun. Ideally the time would have to be equated with the time point that corresponds to the beginning of the elimination.

These problems do not exist with the calculation of blood circulation volume on the basis of a circulation impulse response, since it is independent of the form and the time point of the first passage. It is also, therefore, independent with respect to the injection time point since, according to definition, in the circulation impulse response the indicator introduction occurs in the form of a Dirac impulse at the time point t=0.

In a practical application of the process the calculation of the circulation transport function (g(t)) from the measured dye concentration is carried out with the aid of an iterative, nonlinear adaptation process. Under allowance of a model function $$g(t)=a_m g_m(t)+a_{m+1}g_{m+1}(t)+\ldots+a_n g_n(t)$$

with $$\sum_{i=m}^{n} a_i = 1,$$

in which the individual compartments $a_m g_m$ are described by left-skewed distribution functions, there is repeatedly carried out a recursive convolution according to the equations $$c(t) = c_{bolus}(t) + c_{rez}(t)$$

and $$c_{rez}(t) = k * \int_o^t g(t-u) * c(u)du$$

and the parameters k, $a_m$ as well as the parameters of the distribution function are optimized according to the process of least quadratic deviation. There, at least one compartment $a_1 g_1(t)$ is determined. Further, c(t) is the concentration time course of the indicator dye at any site in the circulation, $c_{bolus}(t)$ the constituent of the first pass of the dye at the measuring site, $c_{rez}(t)$ a recirculating constituent of the dye concentration time course, and k the elimination fraction of the dye eliminated by the liver.

In this calculation process there lies a simplified circulation method which, nevertheless, sufficiently accurately imitates the actual relations. The process is based on the principles of stochastic system analysis, in which there is calculated a circulation transport function for the dye from the recirculation kinetics of the dye.

Preferably two compartments $a_1 g_1(t)$ and $a_2 g_2(t)$ are posited in the calculation of the circulation transport function. This selection is based on previous investigations which have been measured on patients in dye dilution curves. It is a matter here of a rapid compartment and a slow compartment.

According to a first alternative, the optical measurement of the dye concentration resulting in the blood circulation can be performed by fiber-optic measurement in a central vessel. This measuring method is distinguished by high measuring sensitivity with relatively low cost.

Another alternative provides that the optical measurement of the dye concentration resulting in the blood circulation is carried out by means of light-transmission, or reflection measurement, of irradiated light at suitable places of the body, e.g., on a finger, earlobe, nose bridge, cheek mucous membrane or forehead.

The apparatus of the present invention is a device for measuring circulating blood volume with an optical measuring sensor. A computer is connected to the sensor. After a prescribed amount of indicator dye is injected into the circulation blood and the resulting dye concentration in the blood measured, the circulating blood volume is determined either from the given amount of the injected dye and of the dye concentration time course or from the blood volume stream and the mean transit time of the indicator dye determined from the dye concentration time course.

In this connection, the underlying problem lies in developing a device for determining the blood circulation volume in which the entire information content of the optically measured dye-dilution curve is utilized for the calculation of the elimination kinetics. This problem is solved in an apparatus according to the apparatus of the present invention. With regard to the manner of functioning and the advantages of the embodiments of the apparatus, the explanations for the process of the invention are applicable.

BRIEF DESCRIPTION OF THE DRAWINGS

Further development and advantageous embodiments of process and apparatus are yielded from the claims, the following specification and the drawings, with the aid of which the invention is described in detail.

In the drawings.

DESCRIPTION OF THE PREFERRED EMBODIMENT

Figure 1:
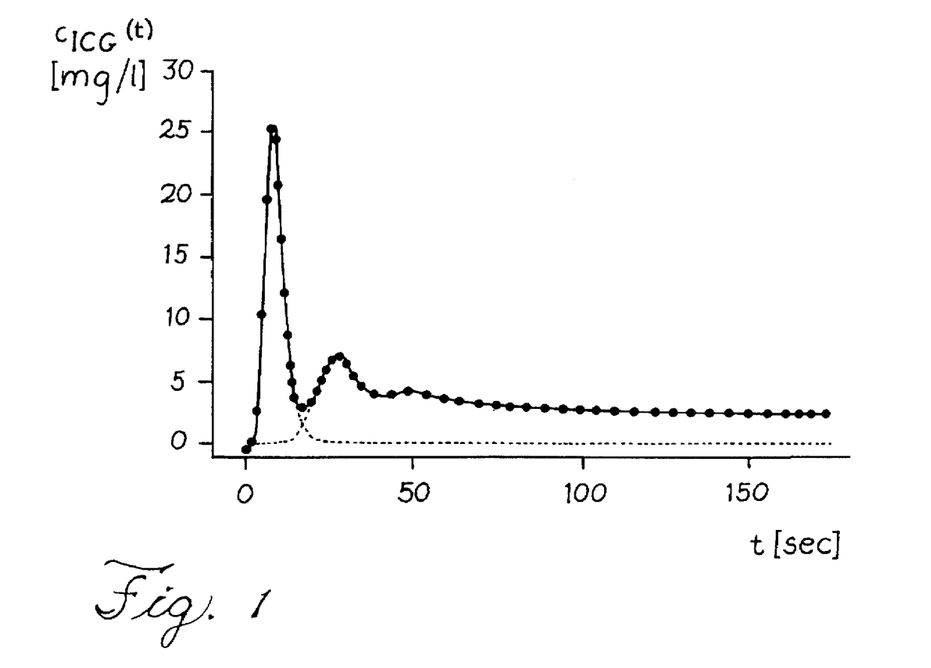
FIG. 1 shows a graphic representation of a concentration time course of an indicator dye.

In FIG. 1 the concentration time course of an indicator dye after an injection into the blood circulation is represented. It is an indicator dilution curve in the case of a bolus injection of 0.2 mg/kg of indocyanine green into the right atrium of the heart, with aortal measurement.

After a first passage of the dye from the injection place through the lung circulation, a rising-again of the concentration is observed which results from the recirculation of the indicator. Only after several circulation passages of the dye can the distribution phase be regarded as concluded. According to previously known processes, it was only afterwards, from the slow, barely visible decline of the indicator concentration, that the elimination kinetics of the dye through the liver could be determined.

Figure 2:
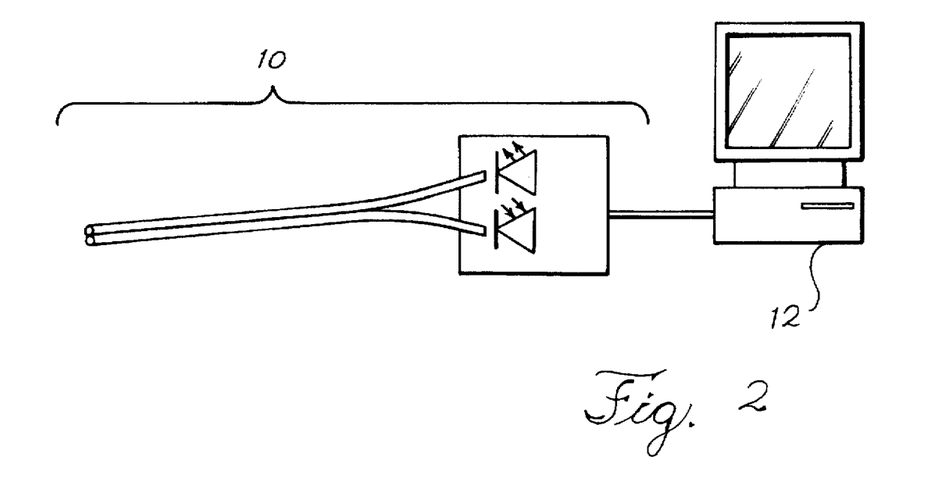
FIG. 2 shows a block circuit diagram of an apparatus for measuring blood circulation volume according to the invention.

In contrast, with the invention the entire information content of the dye dilution curve is evaluated. For this purpose the apparatus represented in FIG. 2 is utilized. It comprises a fiber-optic sensor and a computer connected with it. The fiber-optic sensor is placed in a central blood vessel and records the dye concentration curve immediately after injection of a prescribed amount of indicator dye into the blood circulation.

Figure 6:
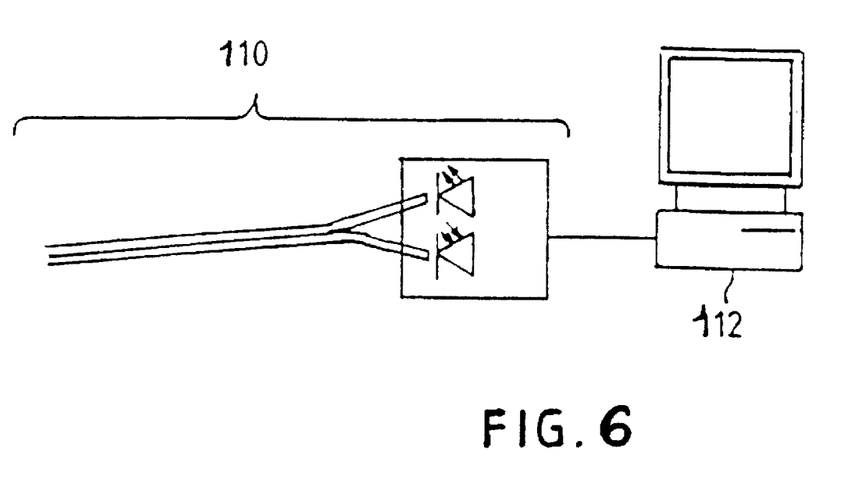
FIG. 6 shows a block diagram of another form of apparatus for measuring blood circulation volume according to the invention.

Alternatively, the apparatus in FIG. 6 may be utilized. It comprises a non-invasive sensor 110 with a computer 112 attached. Light is transmitted through or reflected from a finger, for example, and measured to record the dye concentration curve. From this curve, on the basis of the mode represented in FIG. 3 of the recirculation of an indicator in the circulation, the volume of circulating blood which corresponds to the representation shown in FIG. 1 is determined.

Figure 3:
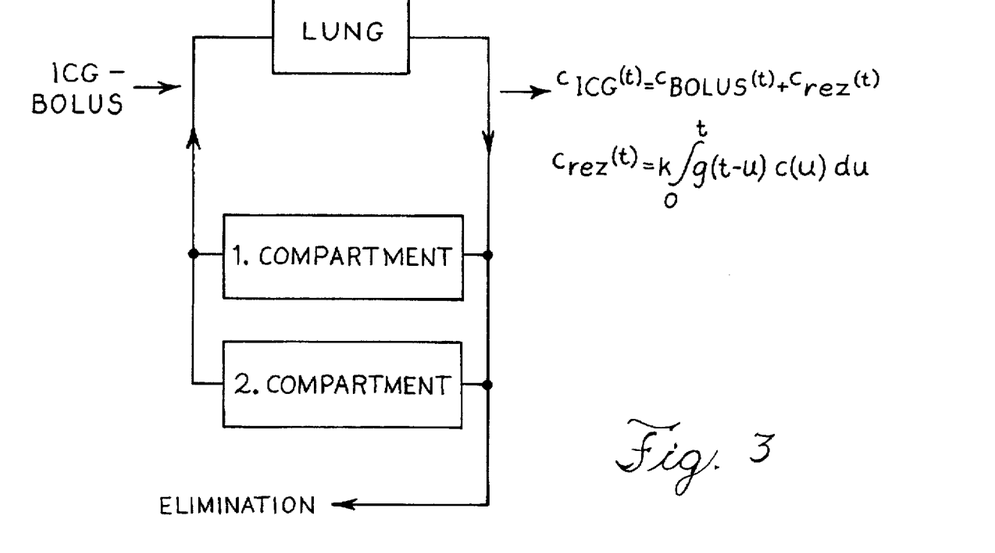
FIG. 3 shows a schematic model for the representation of the recirculation of an indicator in the circulation.

The model shows the transport path of the injected indicator dye ICG as a bolus injection that leads first through the lung. Behind the lung, the transport path divides into a first rapid compartment, a second slow compartment and into an elimination of the dye through the liver. The first and second compartments lead thereupon back to the lung the concentration of the indicator dye at the exit of the lung follows the function:

$$c(t) = c_{bolus}(t) + c_{rez}(t)$$

with $$c_{rez}(t) = k * \int_0^t g(t-u) * c(u)du.$$

Here, $c(t)$ is the concentration time course of the indicator dye, $c_{bolus}(t)$ the first constituent of the dye concentration time course directly passing the measuring place, $c_{rez}(t)$ a recirculating constituent of the dye concentration time course, and $k$ the elimination fraction of the dye eliminated through the liver. $g(t)$ is a transport function which characterizes the transport behavior of the circulation.

The transport process is described by a convolution integral. Recirculation in this manner of representation signifies that the result of the convolution, $C_{rez}(t)$, simultaneously also influences the input function $c(t)$. The recirculation of the indicator leads, therefore, to an interrelation which is described, in principle, as follows:

$$c(t) = f[g(t), c(t)]$$

For $g(t)$ there are posited the compartments of the circulation model. Since previous investigations showed that in dye dilution curves that have been measured on patients, as a rule, for $g(t)$ two compartments are to be posited, there is yielded for the general model function:

$$g(t) = a_m g_m(t) + a_{m+1} g_{m+1}(t) + \ldots + a_n g_n(t)$$

with $$\sum_{i=m}^{n} a_i = 1,$$

in which the individual compartments $a_m g_m$ are described by left-skewed distribution functions, the special expression:

$$g(t) = a_1 g_1(t) + a_2 g_2(t).$$

the calculation of the circulation transport functions from measured dye curves is carried out by the computer with the aid of an iterative, nonlinear adaptation process, in which under allowance of the model function $$g(t) = a_1 g_1(t) + a_2 g_2(t)$$

there is repeatedly carried out a recursive convolution according to the equations $$c(t) = c_{bolus}(t) + c_{rez}(t)$$

and $$c_{rez}(t) = k * \int_0^t g(t-u) * c(u)du$$

in which $k$, $a_1$, $a_2$ and the parameters of the distribution functions are optimized according to the process of the least quadratic deviation.

Figure 4:
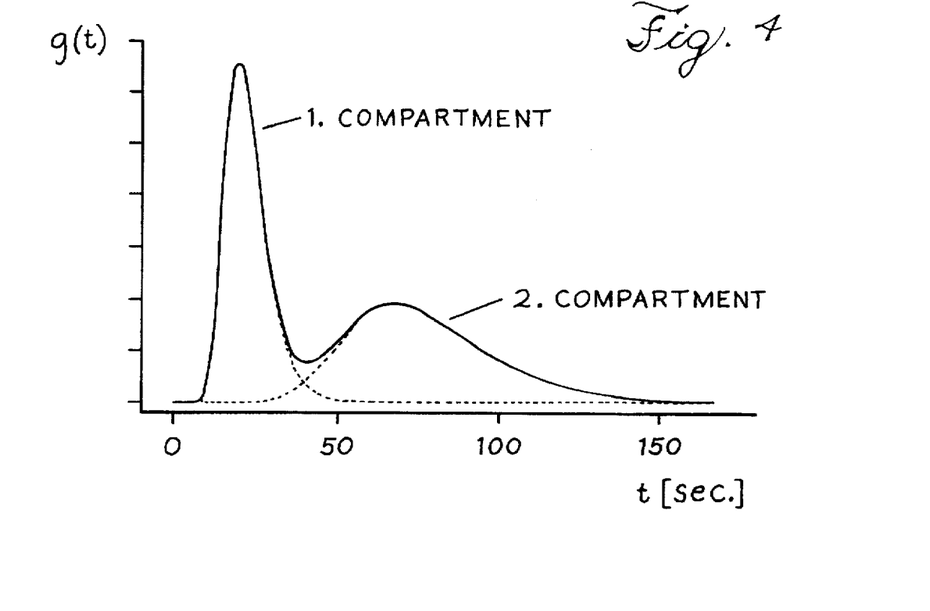
FIG. 4 shows a representation of the circulation transport function.

After execution of these computing steps there is yielded a transport function such as was calculated as an example for the data contained in FIG. 1 for two compartments and is represented in FIG. 4.

Figure 5:
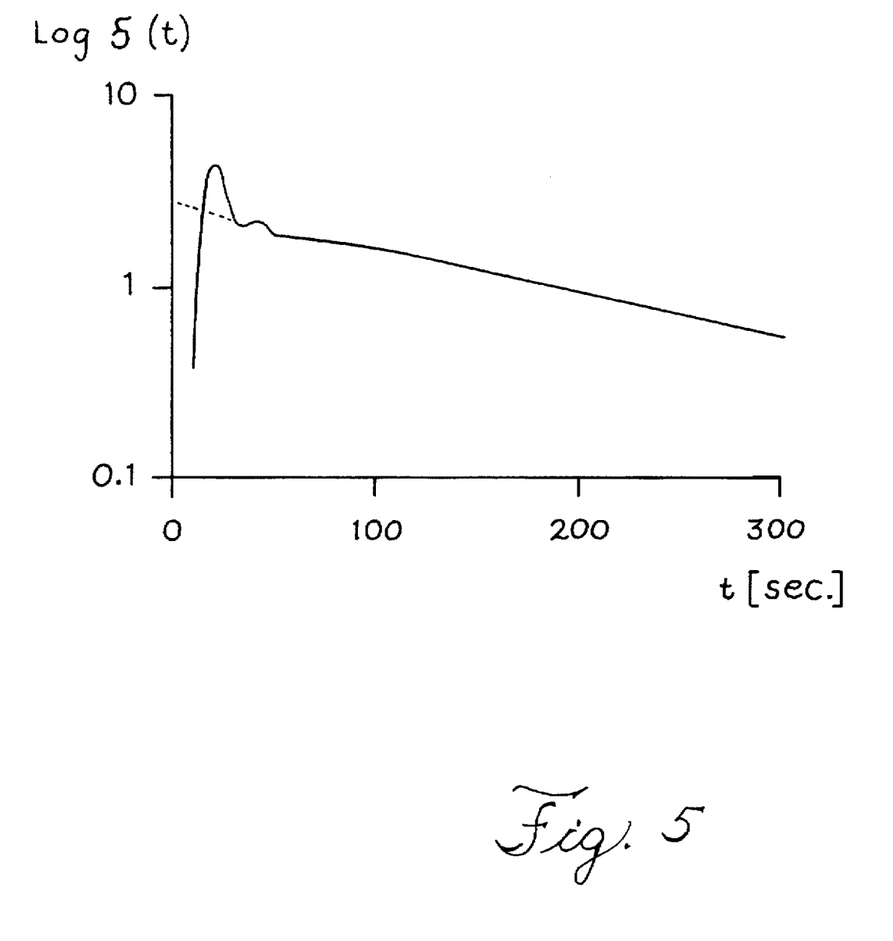
FIG. 5 shows a representation of a typical circulation impulse response.

For the determined circulation transport function there can now be calculated the circulation impulse response that would correspond to an ideal indicator injection in infinitely brief time for the time point t=0. This circulation impulse response is represented in FIG. 5. In semi-logarithmic plotting it presents, after an initial distribution phase in the further course, a monoexponential characteristic which is clearly determined by the parameters of the circulation transport function. It is possible, therefore, in analogy to the conventional process, to determine the virtual concentration $c_0$ at the time point t=0 by monoexponential retro-extrapolation, or by direct calculation from the parameters of the circulation transport function.

There is now yielded the circulating blood volume $V_{d\text{-}Blut}$ from the given amount of the injected indicator dye $m_0$ and the virtual dye concentration $c_0$, at the time point t=0, according to the relation $$V_{d\text{-}Blut} = m_0/c_0.$$

This calculation is made with the same computer with which the data detection for the dye concentration time curves is also performed. With a commercially available MS-DOS computer the evaluation of the dye curves takes only a few seconds, so that the result is available immediately after the measurement.

I claim:

1. A process for determining circulating blood volume $V_d$ in a patient comprising the steps of:

a) injecting a known amount of indicator dye $M_o$ into the circulating blood whereby the dye circulates with the blood and the concentration of dye in the blood varies with time in an indicator dye dilution curve indicative of a dye concentration time course C(t);

b) optically measuring the dye concentration time course C(t) in the circulating blood immediately after injecting the dye;

c) from the concentration time course C(t), calculating the mean transit time $m_{tr}$ which the indicator dye requires in order to pass through a predetermined portion of the circulation;

d) measuring the blood volume flow V in the patient; and e) calculating the blood volume $V_d$ using the equation $V_d = V * m_{tr}$.

2. A process for determining circulating blood volume $V_d$ in a patient whose circulation has a characteristic transport function g(t) and circulation pulse response, comprising the steps of:

a) injecting a known amount of indicator dye $M_o$ into the circulating blood whereby the dye circulates with the blood and the concentration of dye in the blood varies with time in an indicator dye dilution curve to establish a dye concentration time course C(t) for the dye in the circulating blood;

b) optically measuring the dye concentration time course C(t) in the circulating blood immediately after injecting the dye;

c) calculating the circulation transport function g(t) for the patient based on the measured dye concentration time course c(t) using an iterative, nonlinear adaptation process, wherein under allowance of a model function $$g(t) = a_m g_m(t) + a_{m+1} g_{m+1}(t) + \ldots + a_n g_n(t)$$

with $$\sum_{i=m}^{n} a_i = 1,$$

in which the individual compartments $a_m g_m$ are described by left-skewed distribution functions, repeated recursive convolutions are carried out according to the equations $$C(t) = C_{bolus}(t) + C_{rez}(t)$$

and $$C_{rez}(t) = k * \int_o^t g(t-u) * C(u) du,$$

while the parameters k, $a_m$ as well as the parameters of the distribution functions are optimized according to the process of the least quadratic deviation, in which at least one compartment $a_1 g_1(t)$ is posited, and $C_{bolus}(t)$ is the constituent directly passing through the measuring place of the dye concentration time course C(t) and k the elimination fraction of the dye eliminated through the liver;

d) determining the circulation pulse response d(t) which corresponds to an ideal indicator injection in an extremely brief period of time at point t=0 using the circulation transport function g(t);

e) determining a virtual dye concentration $C_o$ at the time point t=0 from the circulation pulse response d(t) by back-extrapolation or direct calculation from the parameters of the circulation transport function g(t), wherein the virtual dye concentration $C_o$ is the hypothetical concentration of dye in the blood if all the dye were injected instantaneously at a time t=0; and f) calculating the blood volume $V_d$ from the known amount of indicator dye and the virtual dye concentration $C_o$ at the time point t=0 according to the relation $V_d = M_o/C_o$.

3. The process according to claim 2, wherein:

a) two compartments $a_g$ and $a_2 g_2$ are posited in the calculation of the circulation transport function.

4. The process according to claims 2, and including the step of:

a) optically measuring the dye concentrationtive course resulting in the circulating blood by fiber-optic measurement in a central vessel.

5. The process according to claim 2, further characterized in that:

a) optically measuring the dye concentration resulting in the blood circulation non-invasively by measuring light-transmission or reflection at a suitable place on the body.

6. A process for determining circulating blood volume $V_d$ in a patient whose circulation has a characteristic transport function g(t) and circulation pulse response, comprising the steps of:

a) injecting a known amount of indicator dye $M_o$ into the circulating blood whereby the dye circulates with the blood and the concentration of dye in the blood varies with time in an indicator dye dilution curve indicative of a dye concentration time course C(t);

b) optically measuring the dye concentration time course C(t) in the circulating blood by fiber-optic measurement in a central vessel immediately after injecting the dye;

c) calculating the circulation transport function g(t) for the patient based on the measured dye concentration time course C(t);

d) determining the circulation pulse response d(t) which corresponds to an ideal indicator injection in an extremely brief period of time at point t=0 using the circulation transport function g(t);

e) determining a virtual dye concentration $C_o$ at the time point t=0 from the circulation pulse response d(t) by back-extrapolation or direct calculation from the parameters of the circulation transport function g(t), wherein the virtual dye concentration $C_o$ is the hypothetical concentration of dye in the blood if all the dye were injected instantaneously at a time t=0; and f) calculating the blood volume $V_d$ from the known amount of indicator dye and the virtual dye concentration $C_o$ at the time point t=0 according to the relation $V_d=M_o/C_o$.

7. A process for determining circulating blood volume $V_d$ in a patient comprising the steps of:

a) injecting a known amount of indicator dye $M_o$ into the circulating blood whereby the dye circulates with the blood and the concentration of dye in the blood varies with time in an indicator dye dilution curve to establish a dye concentration time course C(t) for the dye in the circulating blood;

b) optically measuring the dye concentration time course C(t) in the circulating blood non-invasively by measuring light-transmission or reflection at a suitable place on the body immediately after injecting the dye; and c) calculating the blood volume $V_d$ based upon the circulating time course C(t).

8. A process for determining circulating blood volume $V_d$ in a patient whose circulation has a characteristic transport function g(t) and circulation pulse response, comprising the steps of:

a) injecting a known amount of indicator dye $M_o$ into the circulating blood whereby the dye circulates with the blood and the concentration of dye in the blood varies with time in an indicator dye dilution curve to establish a dye concentration time course C(t) for the dye in the circulating blood;

b) optically measuring the dye concentration time course C(t) in the circulating blood non-invasively by measuring light-transmission or reflection at a suitable place on the body immediately after injecting the dye;

c) calculating the circulation transport function g(t) for the patient based on the measured dye concentration time course C(t);

d) determining the circulation pulse response d(t) which corresponds to an ideal indicator injection in an extremely brief period of time at point t=0 using the circulation transport function g(t);

e) determining a virtual dye concentration $C_o$ at the time point t=0 from the circulation pulse response d(t) by back-extrapolation or direct calculation from the parameters of the circulation transport function g(t), wherein the virtual dye concentration $C_o$ is the hypothetical concentration of dye in the blood if all the dye were injected instantaneously at a time t=0; and f) calculating the blood volume $V_d$ from the known amount of indicator dye and the virtual dye concentration $C_o$ at the time point t=0 according to the relation $V_d=M_o/C_o$.

* * * * *

UNITED STATES PATENT AND TRADEMARK OFFICE
CERTIFICATE OF CORRECTION

PATENT NO.    : 5,687,726
DATED         : November 18, 1997
INVENTOR(S)   : Andreas Hoeft Page 1 of 1

It is certified that error appears in the above-identified patent and that said Letters Patent is hereby corrected as shown below:

Claim 3,
Line 1, please delete "," (comma) after "2".

Claim 4,
Line 1, please change " claims 2, and " to -- claim 2 and --.
Line 3, please change "concentrationtive" to -- concentration time -- .

Claim 5,
Line 1, please change "claim 2, further characterized in that:" to -- claim 2 further including the step of : -- .
Line 3, after "concentration" please insert -- time course -- .

Signed and Sealed this

Fourth Day of September, 2001

*Attest:*

*Attesting Officer*

NICHOLAS P. GODICI
*Acting Director of the United States Patent and Trademark Office*